US006875796B2

(12) United States Patent
Stedronsky

(10) Patent No.: US 6,875,796 B2
(45) Date of Patent: Apr. 5, 2005

(54) METHODS OF USING PRIMER MOLECULES FOR ENHANCING THE MECHANICAL PERFORMANCE OF TISSUE ADHESIVES AND SEALANTS

(75) Inventor: Erwin R. Stedronsky, La Jolla, CA (US)

(73) Assignee: Protein Polymer Technologies, Inc., San Diego, CA (US)

( * ) Notice: Subject to any disclaimer, the term of this patent is extended or adjusted under 35 U.S.C. 154(b) by 0 days.

(21) Appl. No.: 10/443,538

(22) Filed: May 21, 2003

(65) Prior Publication Data

US 2003/0199606 A1 Oct. 23, 2003

Related U.S. Application Data

(63) Continuation of application No. 09/888,225, filed on Jun. 22, 2001, now Pat. No. 6,576,685, which is a continuation of application No. 09/102,521, filed on Jun. 22, 1998, now Pat. No. 6,258,872, which is a continuation-in-part of application No. 08/879,564, filed on Jun. 20, 1997, now Pat. No. 6,015,474.

(51) Int. Cl.$^7$ ............................ C09J 5/04; C09J 189/00; A61K 38/00; A61L 24/10
(52) U.S. Cl. ...................... 523/118; 524/20; 156/314; 156/336; 206/568; 427/2.1; 427/323; 428/420; 428/355 CP; 514/454; 606/214
(58) Field of Search .................... 523/118; 524/20; 156/314, 336; 206/568; 427/2.1, 323; 428/355 CP, 420; 514/454; 606/214

(56) References Cited

U.S. PATENT DOCUMENTS

| | | |
|---|---|---|
| 4,364,473 A | 12/1982 | Bogaert |
| 4,382,792 A | 5/1983 | Smith et al. |
| 4,593,054 A | 6/1986 | Asmussen et al. |
| 4,766,005 A | 8/1988 | Montgomery et al. |
| 4,913,939 A | 4/1990 | Montgomery |
| 5,015,677 A | 5/1991 | Benedict et al. |
| 5,292,362 A | 3/1994 | Bass et al. |
| 5,530,038 A | 6/1996 | Yamamoto et al. |
| 5,552,452 A | 9/1996 | Khadem et al. |
| 5,733,868 A | 3/1998 | Peterson et al. |
| 5,817,303 A | 10/1998 | Stedronsky et al. |
| 6,015,474 A * | 1/2000 | Stedronsky .................. 156/314 |
| 6,183,498 B1 * | 2/2001 | Devore et al. ............... 606/214 |
| 6,258,872 B1 * | 7/2001 | Stedronsky .................. 523/118 |
| 6,576,685 B2 * | 6/2003 | Stedronsky .................. 523/118 |

FOREIGN PATENT DOCUMENTS

WO      WO 93/16687      9/1993

OTHER PUBLICATIONS

Chuck, R.S., et al., "Dye–Enhanced Laser Tissue Welding", *Lasers in Surgery and Medicine* 9:471–477 (1969).
Oz, M.C., et al., "Indocyanine Green Dye–Enhanced Welding with Diode Laser", *Surgical Forum* vol. XL:316–319 (1989).
Oz, M.C., et al., "Tissue soldering by use of Indocyanine green dye–enhanced fibrogen with the near infrared diode laser", *Journal of Vascular Surgery* 11(5):718–725 (1990).
Schober, R., et al., "Laser–Induced Alteration of Collagen Substructure Allows Microsurgical Tissue Welding", *Science*, 232;1421–1422 (1986).
Wider, T.M., et al., "Skin Closure with Dye–Enhanced Laser Welding Fibrinogen", *Plastic and Reconstructive Surgery*, 88(6):1018–102S (1991).

\* cited by examiner

*Primary Examiner*—Peter Szekely
(74) *Attorney, Agent, or Firm*—Dorsey & Whitney LLP; Richard F. Trecartin

(57) ABSTRACT

The present invention concerns novel methods for enhancing the mechanical performance of tissue adhesives and sealants which comprises employing a primer molecule in association with a tissue adhesive or sealant, wherein the primer molecule serves to enhance the strength of the interface between the tissue and the adhesive matrix. The primer molecules described herein function to interact with a protein present in the tissue, thereby altering its characteristics to make it more amenable to bonding with the adhesive matrix. Primer molecules may be applied to the tissue independently from the tissue adhesive or sealant or may be mixed with the tissue adhesive or sealant prior to application to the tissue.

16 Claims, No Drawings

METHODS OF USING PRIMER MOLECULES FOR ENHANCING THE MECHANICAL PERFORMANCE OF TISSUE ADHESIVES AND SEALANTS

This application is a continuation of U.S. application Ser. No. 09/888,225, filed Jun. 22, 2001, U.S. Pat. No. 6,576,685, which is a continuation of U.S. application Ser. No. 09/102,521, filed Jun. 22, 1998, U.S. Pat. No. 6,258,872, which is a continuation-in-part of U.S. application Ser. No. 08/879,564, filed Jun. 20, 1997, U.S. Pat. No. 6,015,474.

FIELD OF THE INVENTION

The present invention is directed to generally applicable methods for using primer molecules to enhance the adhesion of tissue adhesive or tissue sealant compositions to tissues.

BACKGROUND OF THE INVENTION

In many situations, there is a need to bond separated tissues or to seal defects in tissues. Sutures and staples are effective and well established wound and tissue defect closure devices. However, there are surgical techniques where classical repair procedures are unsatisfactory, limited to highly trained specialists (e.g., microsurgery), or not applicable due to tissue or organ fragility, inaccessibility (e.g., endoscopy procedures), or loss of gases or fluids, including capillary "weeping". Tissue adhesives and sealants have been developed to meet these needs. They may be used to seal or reinforce wounds that have been sutured or stapled, as well as finding independent use. The leading commercial products are fibrin glues and cyanoacrylates. However, both products have significant limitations which have prevented their widespread use.

In this regard, one of the major limitations encountered in the development and/or use of tissue adhesive and sealant compositions is their inability to form a sufficiently strong bond to tissues. Therefore, tissue adhesives and sealants may have to be employed in combination with sutures and/or staples so as to reduce the tissue bonding strength required for acceptable performance. As described above, however, there are many indications where the use of sutures and/or staples is undesirable, inappropriate or impossible.

As demonstrated by the Applicants herein, mechanical failure of bonds formed by tissue adhesive and sealant systems may occur at the interface between the crosslinked adhesive matrix and the tissue. The inability of the adhesive matrix to form a strong interface or bond with tissues is most likely due to the fact that various proteins in the tissue are not readily amenable to non-covalent and/or covalent interactions with the tissue adhesive or sealant components as applied and/or during and after curing. For example, collagen present in tissues is a highly aggregated, insoluble protein which, because of its physical characteristics, is not readily amenable to interacting with tissue adhesive or sealant components. The same often holds true for other tissue-associated proteins such as actin and myosin. As a result, for most tissues and adhesive and sealant systems, failures are generally believed to occur at the interface between the crosslinked adhesive matrix and one or more tissue-associated protein such as collagen, actin and myosin.

One possibility for improving the mechanical performance of a tissue adhesive or sealant is to strengthen the interface between a tissue-associated protein and the adhesive matrix by altering the physical characteristics of the adhesive or sealant components to more closely approximate those of protein components of the tissue, thereby making the two components more compatible and amenable to non-covalent and/or covalent interaction. As one example, bonding of a dental restoration to the dentine of a tooth requires the establishment of adhesion between the demineralized collagen present in the dentine and a methacrylate adhesive matrix. In one study, alteration of the vinyl monomers present in a methacrylate adhesive matrix to more closely match the solubility parameter of collagen present in the dentine resulted in an increased strength of bonding of a dental restoration. (Miller, *Adhesive Bonding to Dentin with Isocyanate Copolymers*", Ph.D. Dissertation, University of Missouri—Columbia (1995)). However, the development of physiologically acceptable adhesives and sealants which closely match the characteristics of native collagen has, for the most part, been unsuccessful.

There is, therefore, a need for novel methods for enhancing the adhesion of adhesive or sealant compositions to tissues. More specifically, there is a need for novel methods of strengthening the adhesive matrix/tissue-associated protein interface so as to enhance the mechanical properties of bonds created by tissue adhesives and sealants, wherein those methods are generally applicable to a variety of different tissues and adhesive and sealant systems.

SUMMARY OF THE INVENTION

The present invention provides generally applicable methods for enhancing the mechanical performance of adhesive and sealant systems for use with both soft and hard tissues in vivo. The methods of the present invention are based at least in part upon the demonstration that certain "primer molecules" are capable of interacting with native component(s), particularly protein(s), in tissue, thereby altering the physical characteristics of those components(s) to better match the characteristics of the crosslinked matrix formed by the tissue adhesive or sealant components as applied and/or during and after curing. By causing the physical characteristics of tissue-associated components to better match those of the adhesive or sealant components, one enhances the ability of a tissue adhesive or sealant of interest to form a stronger adhesive matrix/tissue-associated component interface which, in turn, results in stronger attachment of the adhesive matrix to the tissue. The primer molecules described herein are useful with virtually all adhesives or sealants for soft and hard tissues in which the strength of the bond formed thereby is limited by failure at the interface between the adhesive matrix and the tissue.

In accordance with the present invention, novel methods for enhancing the mechanical performance of tissue adhesives and sealants are provided. In one embodiment, the present invention is directed to methods for maintaining separated tissues in proximate relationship which comprise applying to the separated tissues (a) a primer molecule and (b) a tissue adhesive, wherein the primer molecule and the tissue adhesive are applied in an amount effective to maintain the separated tissues in proximate relationship when they are brought into such a relationship. In another embodiment, methods for sealing a defect in a tissue are provided, wherein the methods comprise applying to the defect (a) a primer molecule and (b) a tissue sealant, wherein the primer molecule and the tissue sealant are applied in an amount effective to seal the defect in the tissue. The primer molecules are such that they are capable of physically interacting with one or more proteins present in the tissue, thereby allowing the tissue to form a strong bonded interface with the crosslinked tissue adhesive or sealant (i.e., adhesive matrix). In certain embodiments, the primer molecule may be capable of physically and/or covalently interacting with collagen, actin and/or myosin present in the tissue. The herein described methods are capable of maintaining separated tissue in proximate relationship or sealing a defect in tissue with greater bond strength than when the tissue adhesive or sealant is employed in the absence of a primer molecule. Primer molecules which find use herein include, for example, chaotropic agents, dyes which are capable of staining tissue-associated proteins such as collagen, actin or myosin, proteins, oligopeptides, and the like.

The present invention is also directed to compositions and kits which are useful for maintaining separated tissue in a proximate relationship or sealing a defect in tissue and which comprise a tissue adhesive or sealant and a primer molecule which is capable of physically interacting with a protein present in the tissue, thereby rendering the tissue capable of forming a bonded interface with the crosslinked matrix of the tissue adhesive or sealant.

DETAILED DESCRIPTION OF THE INVENTION

The present invention is directed to generally applicable methods for enhancing the mechanical performance of adhesives and sealants for use with hard and soft tissues, wherein those tissues may be associated with a living organism or otherwise. The methods of the present invention are based at least in part on the demonstration that certain "primer molecules" are capable of interacting with one or more native components in tissue, thereby altering the physical properties of that component to better match the characteristics of the adhesive or sealant components as applied and/or during and after curing. In a preferred embodiment, the tissue component is a protein. Because the protein in the tissue will then possess physical properties (in terms of wettability, swellability, structure, etc.) which enhance the ability of the adhesive or sealant components to non-covalently and/or covalently interact with the altered protein, thereby forming a stronger adhesive matrix/tissue-associated protein interface, a stronger bond of the adhesive matrix to the tissue results. In various preferred embodiments, the tissue-associated protein that interacts with the primer molecule is collagen, actin or myosin.

In this regard, achieving intimate contact between adhesive components and an adherend is required for increasing the strength of adhesive joints (Kaelble, "*Physical Chemistry of Adhesion*", Wiley-Interscience, New York (1971) and Iyengar et al., *Journal of Applied Polymer Science* 11:2311–2324 (1967)). However, wetting and intimate contact of tissue adhesive or sealant components with tissue-associated proteins is often impeded by the insolubility and high degree of aggregation of many of the proteins present in the tissue. Applicants demonstrate herein that primer molecules which interact with tissue-associated proteins are capable of making those proteins more accessible to interaction with the components of a variety of different tissue adhesives and sealants which, in turn, enhances the mechanical performance of these tissue adhesives and sealants.

As such, the term "primer molecule", "primer" and grammatical equivalents thereof as used herein refer generally to molecules which are capable of physically interacting with one or more native proteins present in a tissue and altering at least one of its native physical characteristics, thereby rendering the tissue capable of forming a bonded interface with a tissue adhesive or sealant matrix. By "physically interacting" is meant that the primer molecule comes into actual physical contact with the protein present in the tissue, thereby altering one or more of its native properties. By rendering the tissue "capable of forming a bonded interface" with a tissue adhesive or sealant is meant that after the tissue-associated protein physically interacts with the primer molecule, the tissue is then capable of non-covalently or covalently interacting with the tissue adhesive or sealant components so as to strengthen the interface between the tissue and the crosslinked adhesive matrix. This phrase is intended to encompass situations where the tissue is initially incapable of interacting with the adhesive or sealant components as well as situations where the primer enhances the tissue's initial capability of interacting with the adhesive or sealant components. Thus, a "bonded interface" between a crosslinked adhesive matrix and the tissue may be a result of non-covalent and/or covalent interactions between the crosslinked adhesive matrix and the tissue. Tissue-associated proteins that interact with primer molecules of the present invention include, for example, collagen, actin, myosin, and the like.

In one embodiment, primer molecules which find use in the present invention are capable of altering the degree of hydrogen bonding of collagen molecules to each other, altering the electrostatic or hydrophobic nature of the collagen and/or its degree of hydration, altering its density and/or degree of openness in its structural organization and/or altering its degree of association with other tissue components, thereby rendering it more wettable, swellable or structurally "open". The increased wettability, swellability and/or "openness" of the collagen in the tissue then enhances the tissue's compatibility towards the components of the tissue adhesive or sealant and the ability to non-covalently and/or covalently interact with an adhesive matrix, thereby resulting in a stronger bonded interface. "Stronger bonds" are generally greater than about 1.3-fold stronger than bonds formed by a tissue adhesive or sealant in the absence of a primer molecule in a lap shear tensile test, usually from about 1.3- to 10-fold stronger, more usually from about 1.3-fold to 8-fold stronger, preferably from about 2- to 8-fold stronger and more preferably from about 2.5- to 6-fold stronger.

Primer molecules which find use in the methods of the present invention are numerous and come from diverse classes of different compounds, all of which, however, are capable of interacting with a native protein in a tissue, thereby altering at least one of its native physical characteristics so as to render the tissue more compatible for forming a bonded interface with an adhesive matrix. For example, primer molecules which find use herein include aqueous chaotropic agents such as urea, guanadinium chloride and phosphatidyl choline. Such "chaotropic agents" are compounds known to be capable of disrupting hydrogen bonding in, solubilizing and/or denaturing proteins, including highly ordered proteins such as collagen, thereby rendering those proteins more accessible to interact with the components of a tissue adhesive or sealant which will become crosslinked to form an adhesive matrix.

Other primer molecules which are capable of interacting with native tissue proteins to alter their physical characteristics and, therefore, which find use in the presently described methods include dyes which are capable of staining various tissue components, including collagen, actin and myosin. Examples of such dyes are numerous and well known in the literature directed to histology and the technology of dying leather, cellulose, wood, etc. including, for example, Lille, ed., "*Conn's Biological Stains*", 9th ed., Williams & Wilkins, Baltimore, Md. (1977), Clark, "*Staining Procedures*", 4th ed., Williams & Wilkins, Baltimore, Md. (1981) and Green, *"The Sigma-Aldrich Handbook of Stains, Dyes, & Indicators"*, Aldrich Chemical Company, Inc., Milwaukee, Wis. (1990), each of which is expressly incorporated herein by reference.

In preferred embodiments, the dyes which are employed in the presently described methods are sulfonated aromatic compounds or xanthenes. One related sulfonated aromatic compound, oligo(1-naphthalene sulfonate-co-formaldehyde) has previously been shown to specifically interact with bovine hide collagen (Takata et al., *Hikaku Kagaku* 33(3):151–156 (1987) and *Chemical Abstracts* 108:206608m (1987)). Sulfonated aromatic dyes which find use as primer molecules include, for example (where the appropriate catalogue numbers from the "Catalog Handbook of Fine Chemicals 1996–1997", Aldrich Chemical Company, Inc., Milwaukee, Wis., are shown in parentheses), Brilliant Blue G (Aldrich 20,140-5), Evan's Blue (Aldrich 20,633-4), Chicago Sky Blue 6B (Aldrich 20,138-3), Cibacron Blue 3GA (Sigma C9534), Cibacron Brilliant Yellow 3G-P (Aldrich 22,847-8), Brilliant Blue R (Aldrich 20,140-5), Lissamine Green B (Aldrich 19,958-3), Acid Blue 92 (Aldrich 21,042-0), Cibacron Brilliant Red 3B-A (Aldrich 22,845-1), Acid Red 97 (Aldrich 21,039-0), Trypan Blue (Aldrich 30,264-3), New Coccine (Aldrich 19,973-7), Orange G (Aldrich 86,128-6), Hydroxy Napthol Blue di-sodium salt (Aldrich 21,991-6), Ponceau S (Aldrich 14,119-4), Bordeaux R (Aldrich 20,962-7), Aniline Blue (Aldrich 41, 504-9), Reactive Black 5 (Aldrich 30,645-2), and the like. Xanthene dyes include Eosin Y (Aldrich 11,983-0), Eosin B (Aldrich 86,100-6), Erythrosin B (Aldrich 19,826-9), Rose Bengal (Aldrich 19,825-0), and the like. Sulfonated aromatic compounds and xanthenes which find use may also be devoid of a chromophore in the visible range of wavelengths as long as they function to physically interact with a tissue-associated component such as collagen, actin or myosin. Colors may be removed, especially from the triarylmethyl dyes, via reduction to their leuco-forms using well known techniques. The analogs to azo dyes may be synthesized by means of substituting 1,2-ethanediyl groups for azo linkages present in the colored molecules, also by well known techniques.

In addition to the aromatic sulfonate compounds described above, other compounds which are capable of interacting with tissue-associated proteins and which will find use herein include, for example, aliphatic sulfonates, aromatic or aliphatic sulfates, phosphates and carboxylates, and oligomers and polymers thereof, all of which are commercially available or the synthesis of which is well within the skill level in the art.

Other primer molecules which are capable of interacting with native tissue-associated proteins to alter their physical characteristics and, therefore, which find use in the presently described methods include, for example, mammalian proteins such as fibrinogen, fibronectin and albumin, as well as recombinantly-produced repetitive unit protein polymers such as SELP0K and SELP0K-CS1, wherein the synthesis of the recombinantly-produced repetitive unit protein polymers is described in detail in U.S. Pat. No. 5,243,038, PCT/US89/05016, PCT/US92/09485 and PCT/US96/06229, the disclosures of which are expressly incorporated by reference in their entirety. Such proteins are capable of interacting with tissue-associated proteins as they exist in native tissue and altering at least one of the physical characteristics thereof, thereby allowing the components of a tissue adhesive or sealant to more readily interact with the tissue to form a stronger bonded interface between the crosslinked adhesive matrix and the tissue.

Primer molecules may also comprise oligomeric structures such as oligopeptides, oligonucleotides, oligosaccharides, and the like, as long as they are capable of physically interacting with a tissue-associated protein. For example, oligomeric combinatorial libraries of peptides, nucleotides or saccharides may by prepared using well known chemical or biological combinatorial synthesis techniques and may be screened for the presence of members which function to physically interact with a tissue-associated protein such as collagen, actin, myosin, and the like. See, for example, Owens and Baralle, *EMBO J.* 5(11):2825–2830 (1986). Library members which are identified as being capable of interacting with a tissue-associated protein may be screened in lap shear tensile strength assays to identify those which are useful as primer molecules in the presently described methods. Any experimentation required to identify such primer molecules is routine and well known in the art.

The primer molecules which find use in the present invention inherently interact with one or more tissue-associated protein and may also be modified to interact strongly with components of the adhesive matrix itself, thereby effectively forming a "bridge" between the protein of the tissue and the crosslinked adhesive matrix. For example, acrylate, methacrylate, acrylamide and methacrylamide decorated primer molecules will be effective in improving the interaction between vinyl-based adhesives or sealants and tissue proteins, wherein the interactions may be both ionic and covalent. Additionally, primer molecules which find use herein may be employed either in monomeric or oligomeric, preferably lower oligomeric, form. Such primer molecules are intended to be encompassed by the present invention.

In addition to the above referenced primer molecules, other primer molecules which find use in the presently described methods may be readily identified without undue experimentation on the part of the ordinarily skilled artisan. For example, as disclosed herein, primer molecules which find use in the presently described methods are those compounds which are capable of physically interacting with tissue-associated proteins. Assays designed to screen large numbers of potential compounds for their ability to bind to and/or otherwise interact with native tissue proteins are well known in the art and/or may be routinely devised by those skilled in the art. For example, potential primer molecules which possess a chromophore (such as a dye) or which are modified to possess a chromophore can be screened for their ability to stain either fibrillar collagen or skin coupons. Moreover, such substrates can be treated with potential primer molecules, wherein those that are capable of physically interacting with proteins in the tissue would be expected to result in a substrate that is more highly solvated with water or that displays an altered collagen melting temperature (Nothbohm et al., *J. Prot. Chem.* 11:635–643 (1992) and Grade et al., *J. Biomed. Matr. Res.* 25:799–811 (1991)). Such assays may be routinely employed to identify compounds which are capable of physically interacting with native tissue proteins as they exist in tissue.

Compounds identified as being capable of physically interacting with one or more tissue-associated proteins may then be employed in combination with a tissue adhesive or sealant of interest to determine if those compounds are capable of enhancing the mechanical performance of the tissue adhesive matrix, either by increasing the mechanical strength of the tissue bond and/or by increasing the time that the bond is capable of holding the separated tissue in proximity. Lap shear tensile testing assays designed to test the ability of a molecule to enhance the mechanical performance of a tissue adhesive or sealant are described in detail below. The use of these assays to identify new primer molecules is routine and does not require undue experimentation on the part of the ordinarily skilled artisan.

The primer molecules described herein may be employed in methods for enhancing the mechanical performance of a wide variety of different tissue adhesive and sealant systems. In fact, the performance of virtually any tissue adhesive or sealant system, either presently known or later developed, which is capable of bonding to any anatomical site can benefit from improved contact between the adhesive matrix components and the tissue, and will show enhanced performance if the bond strength of that tissue adhesive or sealant is limited by failure at the interface between the tissue and the adhesive matrix. Such tissue adhesive or sealant systems include the well known methacrylate systems, and the like. Adhesive matrices comprising synthetic polymers such as polyethylene glycol, polyvinylalcohols, polyesters, and the like, including derivatives may also find use in combination with a suitable crosslinking agent. In one embodiment, the adhesive matrix of the tissue adhesive or sealant employed may also comprise either natural or recombinantly-produced protein or combinations thereof, wherein those proteins are capable of being crosslinked by a suitable crosslinking agent to form an adhesive matrix. Natural proteins which find use for incorporation into a tissue adhesive or sealant include, for example, gelatin (with or without resorcinol), fibrin, fibrinogen, albumin, casein, silk fibroin, keratin, mussel adhesive protein, collagen, succinylated gelatin derivatized with cystein, as well as a variety of other well known natural proteins that are useful for adhesive or sealant purposes.

In addition to the natural proteins described above, various recombinantly-produced proteins may also find use in tissue adhesives and sealants. Not only may the natural proteins described above be recombinantly produced, but also various crosslinkable non-natural recombinant proteins will find use herein. Preferred non-natural recombinantly produced proteins include proteins which comprise repeating units of naturally occurring amino acid sequence blocks from such naturally occurring structural proteins as fibroin, elastin, collagen, keratin, and the like. The recombinant preparation of these non-natural repetitive unit proteins is described in detail in U.S. Pat. No. 5,243,038, PCT/US89/05016 (WO 90/05177), PCT/US92/09485 (WO 93/10154) and PCT/US96/06229 (WO 94/34618) (the disclosures of which are expressly incorporated herein by reference in their entirety), wherein the adhesive and crosslinking properties of these proteins are also discussed. Preferred repetitive unit proteins for use in the presently described methods include SELP8K, SELP0K-CS1 and SELP0K, whose preparation and amino acid sequences are described in PCT/US96/06229 (WO 94/34618).

The proteins described above will be capable of being crosslinked to form an adhesive matrix. For crosslinking purposes, these proteins will comprise one or more reactive functionalities, generally present on one or more amino acids of the protein, and may include such functionalities as amino, e.g., lysine, carboxyl, e.g., aspartate and glutamate, guanidine, e.g., arginine, hydroxyl, e.g., serine and threonine, and thiol, e.g., cysteine. Pendant groups may also be employed to provide the desired functionalities. For example, carboxy groups may be reacted with polyamines so as to exchange a carboxyl functionality for a single amino or plurality of amino groups. An amino group may be substituted with a polycarboxylic acid, so that the amino group will be replaced with a plurality of carboxylic acid groups. A thiol may be replaced with an aldehyde, by reaction with an aldehydic olefin, e.g. acrolein, so as to provide for an aldehyde functionality. Other functionalities which may be introduced for crosslinking purposes may include, for example, phosphate esters, activated olefins, e.g., maleimido, thioisocyanato, and the like as well as other reactive functionalitites which are known in the art. By appropriate choice of the reactive functionalities on the protein and the crosslinking agent (see below), the rate of reaction and the degree of crosslinking can be controlled.

In order to crosslink the above described proteins for the purpose of forming an adhesive matrix, various chemical and/or enzymatic crosslinkers which have been used previously and have been found to be physiologically acceptable may find use. Various reactive functionalities may be employed, such as aldehyde, isocyanate, mixed carboxylic acid anhydride, e.g. ethoxycarbonyl anhydride, activated olefin, activated halo, amino, and the like. Preferred chemical crosslinkers include dialdehydes, such as glutaraldehyde, formaldehyde, activated diolefins, diisocyanates such as tetramethylene diisocyanate, hexamethylene diisocyanate, octamethylene diisocyanate, 1,6-diisocyanatohexane (HMDI), 4-isocyanatomethylphenyl-3-isocyanatopropanate (IMP), acid anhydrides, such as succinic acid anhydride, ethylene diamine tetraacetic acid dianhydride, diamines, such as hexamethylene diamine, cyclo(L-lysyl-L-lysine), L-lysine, and the like. The crosslinking agent may be a free radical, initiating vinyl polymerization, such as a mixture of a tertiary amine and eosin B, which is light activated, a tertiary amine and a persulfate, which is thermally activated, and the like. The crosslinking agent may also contain unsymmetrical functionalities, for example, activated olefin aldehydes, e.g., acrolein and quinoid aldehydes, activated halocarboxylic acid anhydride, and the like. The crosslinking agents will usually be commercially available or may be readily synthesized in accordance with conventional ways, either prior to application of the adhesive or sealant or by synthesis in situ.

Enzymatic crosslinkers may also find use in the presently described methods. Examples of such enzymatic crosslinkers which find use in the present invention include, for example, tyrosine oxidase, lysyl oxidase, phosphorylases, such as cellular phosphorylase A or B, glycosylases, and fatty acyltransferases. Transamidases are preferred, particularly transglutaminases, specifically liver, muscle, epithelial or keratinocyte transglutaminases and Factor XIII.

Thus, as used herein, the phrase "tissue adhesive" refers to a composition which may be employed independently to bond tissues together. The phrase "tissue sealant" refers to the same or different composition or formulation which may be employed to seal defects in tissues, created surgically or otherwise. The use of adhesive substrates and crosslinkers to prepare a tissue adhesive or sealant for use in the presently claimed invention is known in the art. Moreover, tissue adhesives and sealants are known in the art, all of which are encompassed for use in the present invention.

The methods of the present invention may be practiced by applying the tissue adhesive or sealant and the primer molecule to the tissue of interest wherein the tissue adhesive or sealant and primer molecule are combined prior to applying the mixture to the tissue. Alternatively, the primer molecule or the tissue adhesive or sealant may be applied to the tissue followed by subsequent application of the tissue adhesive or sealant or primer molecule, respectively. In a preferred embodiment, the primer molecule-is first applied to the tissue, thereby allowing the primer molecule to interact with one or more proteins present in the tissue, followed by subsequent application of the tissue adhesive or sealant. The crosslinking agent may be applied in combination with the other components of the tissue adhesive or sealant or may be applied independently.

The tissue adhesive or sealant components and the primer molecules may be applied to the tissue in any convenient way, for example by using a syringe, catheter, cannula, manually applying the compositions, spraying, or the like. If used as an adhesive, the compositions may be applied prior to or after the time that the tissue segments are brought into proximate relationship.

Further details of the invention are illustrated in the following non-limiting examples.

Materials and Methods

1. Recombinant Preparation of Repetitive Unit Protein Polymers

The construction of large synthetic DNA and its use in the recombinant preparation of a variety of different repetitive unit protein polymers has been described in U.S. Pat. No. 5,243,038, PCT/US89/05016 (WO 90/05177), PCT/US92/09485 (WO 93/10154), and PCT/US96/06229 (WO 94/34618), the disclosures of which are expressly incorporated herein by reference in their entirety.

2. Preparation of Test Coupons

A. Preparation of Rat Skin Test Coupons [CP1]

Hides were collected from freshly sacrificed (250–300 g) female Sprague-Dawley rats. Freshly harvested hides were interleaved between layers of gauze soaked in phosphate buffered saline (PBS), placed in a sealed plastic bag, and stored in a freezer at −20° C. Hides were thawed approximately 30–60 minutes prior to use. Thawing was accomplished by using natural convection at room temperature or by placing the sealed bag of hides in a water bath at 40° C. Thawed hides were cut with a standard single-edged razor blade into 1 cm×3 cm coupons, and then aggressively scraped with a razor blade to remove all fascia and loose muscle Coupons were interleaved between gauze soaked in PBS and placed in sealed plastic bags. The sealed bags were either placed in an ice bath for short term storage or were placed in a −20° C. freezer for long term storage. Thawing prior to use was accomplished as described above for whole hides.

B. Preparation of Myocardium Test Coupons [CP2]

Fresh bovine hearts were obtained from an abattoir, rinsed with PBS, and stored frozen until use. The frozen heart was allowed to partially thaw at room temperature, and was cut into slabs about 2 mm thick using a standard meat slicer. Slabs were cut with a standard single edged razor blade into 1 cm×3 cm coupons, interleaved between gauze soaked in PBS, and placed in sealed plastic bags. The sealed bag was placed in an ice bath for short term storage. No long term storage of myocardium coupons was attempted. Myocardium displays a pronounced direction to the alignment of the muscle fibers. Test coupons were cut relative to this alignment: [CP2p] longitudinal coupons were cut with the long axis of the coupon parallel to the muscle fiber axis; [CP2t] transverse coupons were cut with the long axis of the coupon perpendicular to the muscle fiber axis; [CP2d] diagonal coupons were cut with the long axis of the coupon at 45° to the muscle fiber axis.

C. Bone Test Coupons [CP3]

Fresh bovine knee joints were obtained from an abattoir, rinsed with PBS, and stored refrigerated until use. Slabs of cancellous bone 2 mm thick were cut from the head of the femur using a fine toothed saw. The slabs were trimmed into coupons 1 cm×2 cm. One end of each coupon, ca. 1 cm×1 cm, was reduced in thickness to about 1 mm using a file. Bone test coupons were interleaved between gauze soaked in PBS, and placed in sealed plastic bags. The sealed bag was placed in an ice bath for short term storage. No long term storage of bone coupons was attempted. The stepped shape described for these test coupons permitted the tensile pull in the Instron testing to occur in line with the axis of the lap joint.

D. Tendon Test Coupons [CP4]

Fresh bovine knee joints were obtained from an abattoir, rinsed with PBS, and stored refrigerated until use. Tendon was dissected from the joint and trimmed into coupons 2 cm long×0.8 cm wide×0.1 cm thick with the long axis of the coupon parallel to the long axis of the tendon. Tendon test coupons were interleaved between gauze soaked in PBS, and placed in sealed plastic bags. The sealed bag was placed in an ice bath for short term storage. No long term storage of tendon coupons was attempted.

E. Articular Cartilage Test Coupons [CP5]

Fresh bovine knee joints were obtained from an abattoir, rinsed with PBS, and stored refrigerated until use. Articular cartilage was dissected from the joint and trimmed into coupons 2 cm long×1 cm wide×0.05 cm thick. Articular cartilage test coupons were interleaved between gauze soaked in PBS, and placed in sealed plastic bags. The sealed bag was placed in an ice bath for short term storage. No long term storage of articular cartilage coupons was attempted.

The mechanics of a lap shear tensile test are such that the maximum strength observed with a given adhesive is dependent upon the mechanical compliance of the adherend coupons used in the test, with stiffer coupons exhibiting a greater apparent strength to failure (Kendall, "Adhesion 2," Edited by K. Allen, Applied Science Publishers, London, p. 121, (1978) and Kendall, *Journal of Physics, D: Applied Physics,* 8:512 (1975)). Consequently, coupons for a related set of tests were selected to be as consistent as possible, especially with respect to thickness. Minimizing variance in the compliance of the test coupons serves to minimize the coefficient of variation observed in a given set of tests, thereby making it possible to discern effects due to changes in the performance of the adhesive.

3. Estimation of Liquid Densities

About 1.0 ml of liquid to be tested was drawn into 1.00 mL tuberculin syringe, the syringe inverted, and the plunger depressed to eject all liquid from the syringe, leaving the Luer hub and needle full of liquid (no air bubbles), and the wetted assembly tared. The syringe was filled to the 1.00 mL mark with the liquid to be tested, the gross weight of the filled syringe was measured, the net weight of the 1.00 mL increment of liquid was calculated, and the density of the liquid was recorded in g/mL. This process was repeated five times, and the mean of these values was used as the estimate of the density of the liquid. Densities of dope solutions and crosslinkers are used in calculations of stoichiometries in several of the adhesive systems and application techniques described below.

4. Crosslinking Agents

The following crosslinking agents were employed:

Glutaraldehyde [GA]: Glutaraldehyde (50% w/w, Fisher G151-1) was distilled and diluted with deionized water to a concentration of 25% (w/w), and stored at 4° C. (Whipple et al., *Journal of Organic Chemistry,* 39(12):1666–1669 (1974) and Hardy et al., *Journal of the Chemical Society, Chemical Communications,* pp. 565–566 (1969)). The density of this solution was estimated as 1.058 g/mL.

Formaldehyde [FA]: Formaldehyde (37% w/w, Aldrich 25,254-9) was used as received. The density of this solution was estimated as 1.110 g/mL 1,6-Diisocyanatohexane [HMDI]: 1,6-Diisocyanatohexane (Aldrich, D12,470-2) was used as received. Product literature specifies its density as 1.040 g/mL.

4-Isocyanatomethylphenyl-3-isocyantopropanate [IMP]: To a mixture of 4-hydroxy-phenylacetic acid (76 g, 0.50 mole) and succinic anhydride (50 g, 0.50 mole) in chloroform (400 mL), triethylamine (101.2 g, 1.00 mole) was added dropwise at a rate to control the exotherm. After the initial exothermic reaction subsided, the mixture was refluxed for 2 hours; FTIR (CHCl$_3$)1759 cm$^{-1}$, 1598 cm$^{-1}$. The reaction mixture was cooled in an ice bath and thionyl chloride (136.8 g, 1.15 mole) was added dropwise over 90 minutes. The reaction mixture was stirred 30 minutes without heating and then refluxed for 2 hours. Solvents were evaporated at reduced pressure using a rotary evaporator. Toluene (150 mL) was added and the white precipitate was filtered, giving a light brown clear solution. This solution was diluted with additional toluene (100 mL) and added dropwise over 4 hours to a mixture of sodium azide (65 g, 1.0 mole) in toluene (50 mL) heated in an oil bath at 120° C. Heating at 120° C. was continued for an additional 4 hours. The mixture was cooled to room temperature and filtered. Toluene was removed from the filtrate by evaporation on the vacuum line. The residue was subjected to distillation at reduced pressure using a wide bore short path distillation head. Product distilled as a yellow-amber viscous liquid (6.09 g, 0.025 mole, 5.0%) between 100° @ 20 mTorr and 120° @ 35 mTorr. $^1$H nmr (CDCl$_3$) δ 7.34(d,2H), 7.12 (d, 2H), 4.50 (s, 2H), 3.71 (t,2H), 2.87 (t,2H); FTIR (neat) $v_{NCO}$ 2272 cm$^{-1}$, $v_{C=O}$ 1760 cm$^{-1}$. The density this product was estimated as 1.236 g/mL.

The dimethylamine adduct was formed by adding dimethylamine (1.0 mL of 2.0 M solution in THF) to 4-isocyanatomethylphenyl-3-isocyantopropanate (0.25 g, 1.0 mmole) in anhydrous diethyl ether (1.0 mL) cooled in an ice bath. The mixture was stirred for 30 minutes in the ice bath and for 30 minutes at room temperature. Anhydrous diethyl ether (5.0 mL) was added, stirred 5 minutes, and the white precipitate filtered, washed with diethyl ether, and dried in vacuum. FTIR (KBr) 3325 cm$^{-1}$, 1754 cm$^{-1}$, 1635 cm$^{-1}$; ES MS m/z=337 (M-H$^+$).

Factor XIIIa [F XIIIa]: Factor XIIIa was prepared as in [PD6] (see below) from the TISSEEL® Kit VH, 2-Component Fibrin Sealant (HUMAN), Vapor Heated, 1.0 mL. [IMMUNO (Canada) Ltd., Catalog No. P199859506S]

5. Preparation of Dopes

Gelatin-Resorcinol-Glutaraldehyde (GRG) Dope [PD1]: Gelatin (200 mg, type B, 225 bloom, Sigma, Cat. No. G9382) and resorcinol (20 mg, Aldrich 30,752-1) were placed in a 100 mm×12 mm test tube and vortexed with 2.0 mL of deionized water until dissolved. The use of a GRG dope is reported by Johnson, U.S. Pat. No. 5,292,333, issued on Mar. 8, 1994.

Gelatin-Resorcinol-Formaldehyde (GRF) Dope [PD2]: Resorcinol (13.5 g, Aldrich 30,752-1) and 43.5 mL of deionized water were placed into a round bottom flask fitted with a mechanical stirrer and heated to 45° C. in a water bath. Gelatin (40.5 g, type B, 225 bloom, Sigma, Cat. No. G9382) was added in portions over a 4 hour period, and the mixture stirred for an additional 16 hours. The use of a GRF dope is reported by Vandor et al., *Zeit. Exper. Chirurg.*, 13: 43–51 (1980) and Koehnlein et al., *Surgery*, 66:377–382 (1966).

SELP8K Dope [PD3]: Protein polymer SELP8K (100 mg) and 1.0 mL of deionized water was placed in an 2.0 mL Eppendorf® tube and vortexed until dissolved. Using a 2 mm glass rod, an aliquot of this dope was streaked across E. Merck colorpHast® test paper, pH range 0–14. The hydrogen ion concentration of this dope was estimated as between pH 7.5–8.0.

SELP0K-CS1 Dope [PD4]: Protein polymer SELP0K-CS1 was used to prepare this dope as a 17% (w/w) solution in water. For example, SELP0K-CS1 (2.028 g) and deionized water (9.205 g, 18 MΩ) water were vortexed in a 15 mL centrifuge tube until homogeneous. Hydrochloric acid (5 μl, 3.6% w/w) was added to the dope, the solution vortexed, and then centrifuged to coalesce bubbles. The density of this dope is estimated as 1.04 g/mL. Dope [PD4] (0.20 mL) was added to deionized water (3.20 mL, 18 MΩ) to prepare a solution with a final concentration of 10.4 mg/mL, and the hydrogen ion concentration was measured using a Radiometer Copenhagen PHM 93 reference pH meter. The goal was to achieve pH=8.3±0.1 for this diluted solution of dope. In the event the pH fell outside of the desired range, further increments of hydrochloric acid (3.6% w/w) or sodium hydroxide (2.0% w/w) were added to the concentrated dope and the dilution and measurement process repeated.

Subsequent preparations of this dope were made with protein polymer SELP0K-CS1 and varied slightly in final pH [pH] (pH=8.37), (pH=8.29), (pH=8.20), (pH=8.26), (pH=8.26), (pH=8.28), and (pH=8.31).

SELP0K-CS1 Dope [PD5]: Protein polymer SELP0K-CS1(1.67 g) and deionized water (7.597 g, 18 MΩ) water were vortexed in a 15 mL centrifuge tube until homogeneous. Hydrochloric acid (33 μl, 3.6% w/w) was added to the dope, the solution vortexed, and then centrifuged to coalesce bubbles. The density of this dope is estimated as 1.04 g/mL. Dope [PD5] (0.20 mL) was added to deionized water (3.20 mL, 18 MΩ) to prepare a solution with a final concentration of 10.4 mg/mL, and the hydrogen ion concentration was measured using a Radiometer Copenhagen PHM 93 reference pH meter as pH=7.27.

TISSEEL® [PD6]: All operations of this procedure were performed in the 37° C. warm room. The lyophilized TISSEEL® and the aprotinin solution from the kit were equilibrated to 37° C. for 30 minutes before adding the aprotinin solution to the TISSEEL®. The mixture was allowed to stand for 5 minutes, swirled briefly, and stirred on a magnetic stirrer for 15 minutes. The mixture was stored at 37° C. until used. The calcium chloride solution supplied with the kit was transferred into the lyophilized Thrombin 4, swirled briefly, and stored at 37° C. until used (the preparation of these solutions was per manufacturer's instructions; TISSEEL KIT VH, 2-Component Fibrin Sealant (HUMAN), Vapor Heated, 1.0 mL; IMMUNO (Canada) Ltd., Catalog # P199859506S).

SELP0K-CS1 Dope [PD7]: Protein polymer SELP0K-CS1(1.91 g) and deionized water (8.675 g, 18 MΩ) were vortexed in a 15 mL centrifuge tube until homogeneous. Hydrochloric acid (18 μl, 3.6% w/w) was added to the dope, the solution vortexed, and then centrifuged. The density of this dope is estimated as 1.04 g/mL. Dope [PD7] (0.20 mL) was added to deionized water (3.20 mL, 18 MΩ) to prepare a solution with a final concentration of 10.4 mg/mL, and the hydrogen ion concentration was measured using a Radiometer Copenhagen PHM 93 reference pH meter as pH=8.30.

SELP0K-CS1 Dope [PD8]: Dope [PD7] (0.36 mL, 0.3715 g) was added by syringe into a 2 mL cryogenic tube. Brilliant Blue G (3.7 mg, [P1]) was added and dissolved by vortexing for one minute.

SELP0K-CS1 Dope [PD9]: Protein polymer SELP0K-CS1 (1.6 grams) and deionized water (7.25 grams, 18 MW) were vortexed in a 15 ml centrifuge tube until homogeneous.

Hydrochloric acid (55 μl, 4.4% w/w) was added to the dope, the solution vortexed, and then centrifuged. The density of this dope is estimated as 1.04 g/ml. Dope [PD9] (0.2 ml) was added to deionized water (3.2 ml, 18 MW) to prepare a solution with a final concentration of 10.4 mg/ml, and the hydrogen ion concentration was measured using a Radiometer Copenhagen PHM 93 reference pH meter as pH=8.24.

SELP0K-CS1 Dope [PD10]: Protein polymer SELP0K-CS1 (1.59 grams) and deionized water (7.43 grams, 18 MW) were used to prepare a dope cognate to [PD9]. Dope [PD10] (0.2 ml) was added to deionized water (3.2 ml, 18 MW) to prepare a solution with a final concentration of 10.4 mg/ml, and the hydrogen ion concentration was measured using a Radiometer Copenhagen PHM 93 reference pH meter as pH=7.4.

SELP0K-CS1 Dope [PD11]: Protein polymer SELP0K-CS1 (1.49 grams) and deionized water (6.971 grams, 18 MW) were vortexed in a 15 ml centrifuge tube until homogeneous. Hydrochloric acid (42 μl, 4.4% w/w) was added to the dope, the solution vortexed, and then centrifuged. The density of this dope is estimated as 1.04 g/ml. Dope [PD11] (0.2 ml) was added to deionized water (3.2 ml, 18 MW) to prepare a solution with a final concentration of 10.4 mg/ml, and the hydrogen ion concentration was measured using a Radiometer Copenhagen PHM 93 reference pH meter as pH=8.00.

6. Preparation of Primer Solutions

[PP1]: Using a four place analytical balance, primers (10 mg±0.3 mg) were weighed into 2 mL cryogenic tubes, the required amount of 100 mM sodium chloride solution added to bring them up at 1% w/w, and the mixture vortexed for 2 minutes. Solutions of primers were prepared just prior to application.

[PP2]: Using a four place analytical balance, primers (10 mg±0.3 mg) were weighed into 2 mL cryogenic tubes, the required amount of 100 mM sodium chloride solution added to bring them up at 5% w/w, and the mixture vortexed for 2 minutes. Solutions of primers were prepared just prior to application.

[PP3]: Protein polymer SELP0K-CS1 dope [PD4] (pH=8.28) was used as primer.

[PP4]: Protein polymer SELP0K-CS1 dope [PD4] (0.40 mL) was diluted with deionized water (0.28 mL, 18 MΩ) to prepare a 10% w/v solution.

[PP5]: Primer solution [PP4] (0.20 mL) was diluted with deionized water (0.20 mL, 18 MΩ) to prepare a 5% w/v solution.

[PP6]: Primer solution [PP4] (0.10 mL) was diluted with deionized water (0.40 mL, 18 MΩ) to prepare a 1% w/v solution.

[PP7]: Approximately 2M aqueous urea was prepared as a primer. Urea (60 g, 1.00 mole) was added to a 100 mL volumetric flask and deionized water (18 MΩ) was added to the mark, and the mixture agitated until dissolved to yield a 10 M stock solution. An aliquot (4.00 mL) of 10 M stock was diluted with deionized water (6.00 mL, 18 MΩ) and adjusted to pH=7.2 by the addition of about 30 μL of concentrated hydrochloric acid to yield an approximately 4M stock solution. An aliquot of 4M stock (0.50 mL) was diluted with deionized water (0.50 mL, 18 MΩ) to yield an approximately 2M solution.

[PP8]: Tisseel® was dissolved in a solution of aprotinin as prepared in [PD6].

[PP9]: Primer [P1; see below] was added directly into the adhesive dope as described in the preparation of [PD8]. No separate priming step was used.

[PP10]: Using a four place analytical balance, primers (100 mg±1 mg) were weighed into 2 ml cryogenic tubes, the required amount of 100 mM sodium chloride solution added to bring them up to 10% w/w, and the mixture vortexed for 2 minutes. Solutions of the primers were prepared just prior to application.

7. Identification of Primer Molecules

A key of primer molecules, their color index number (for the dyes), manufacturer, and catalog number follows:

| | | |
|---|---|---|
| [P1]: | Brilliant Blue G (CI# 42655) | Aldrich 20, 140-5 |
| [P2]: | Evan's Blue (CI# 23860) | Aldrich 20, 633-4 |
| [P3]: | Chicago Sky Blue 6B (CI# 24410) | Aldrich 20, 138-3 |
| [P4]: | Cibacron Blue 3GA (CA# 12236-82-7) | Sigma C9534 |
| [P5]: | Cibacron Brilliant Yellow 3G-P (CI# 18972) | Aldrich 22, 847-8 |
| [P6]: | Brilliant Blue R (CI# 42660) | Aldrich 20, 140-5 |
| [P7]: | Lissamine Green B (CI# 44090) | Aldrich 19, 958-3 |
| [P8]: | Acid Blue 92 (CI# 13390) | Aldrich 21, 042-0 |
| [P9]: | Cibacron Brilliant Red 3B-A (CI# 18105) | Aldrich 22, 845-1 |
| [P10]: | Acid Red 97 (CI# 22890) | Aldrich 21, 039-0 |
| [P11]: | Trypan Blue (CI# 23850) | Aldrich 30, 264-3 |
| [P12]: | New Coccine (CI# 16255) | Aldrich 19, 973-7 |
| [P18]: | Orange G (CI# 16230) | Aldrich 86, 128-6 |
| [P19]: | Urea | Aldrich 20, 888-4 |
| [P20]: | Tisseel® Fibrinogen | IMMUNO, Ltd., # P199859506S |
| [P21]: | SELP0K-CS1 | n/a |
| [P22]: | Fosin Y (CI# 45380) | Aldrich 11, 983-0 |
| [P23]: | Eosin B (CI# 45400) | Aldrich 86, 100-6 |
| [P24]: | Erythrosin B (CI# 45430) | Aldrich 19, 826-9 |
| [P25]: | Rose Bengal (CI# 45440) | Aldrich 19, 825-0 |

8. Application of Primer Molecules to Test Coupons

[AP1]: All operations of this procedure were performed in the 37° C. warm room. Test coupons were placed on a glass plate and covered with a sheet of plastic film while they equilibrated to 37° C. Primer solution (5 μL) was applied to each coupon of the adhesive joint using a P-20 Pipetman®. Care was taken to distribute the primer solution uniformly over the 1 cm×1 cm area intended for the joint. The primer solution was allowed to set on the coupon for 1–2 minutes before the excess was blotted off using an adsorbent tissue paper.

[AP2]: Cognate to [AP1] except 10 μl of primer solution was applied per coupon.

[AP3]: All operations of this procedure were conducted at ambient room temperature of approximately 23° C. Test coupons were placed on a glass plate and covered with a sheet of plastic film while they equilibrated to room temperature. Primer solution (5 μL) was applied to each coupon of the adhesive joint using a P-20 Pipetman®. Care was taken to distribute the primer solution uniformly over the 1 cm×1 cm area intended for the joint. The primer solution was allowed to set on the coupon for 2–3 minutes before the excess was blotted off using an adsorbent tissue paper.

[AP4]: All operations of this procedure were conducted in a 37° C. warm room. Test coupons were placed on a glass plate and covered with a sheet of plastic film while they equilibrated to 37° C. Primer solution (5 μL) was applied to each coupon of the adhesive joint using a P-20 Pipetman®. Care was taken to distribute the primer solution uniformly over the 1 cm×1 cm area intended for the joint. The primer solution was allowed to set on the coupon for 2–3 minutes before the excess was blotted off using an adsorbent tissue paper.

[AP5]: All operations of this procedure were conducted in a 37° C. warm room. Test coupons were placed on a glass plate and covered with plastic film while they equilibrated to 37° C. Primer solution (15 μL) was applied to each coupon of the adhesive joint using a P-20 Pipetman®. Care was taken to distribute the primer solution uniformly over the 1 cm×1 cm area intended for the joint. The primer solution was aggressively worked into the surface of each coupon using 30–40 strokes with a flat bladed stainless steel spatula.

[AP6]: Cognate to [AP5] except 5 μl of primer solution was applied per coupon.

[AP7]: Primer was added directly to the dope preparation [PD8]. No separate application of primer was used.

[AP8]: Cognate to [AP3] except that the primer was allowed to set for 5–10 minutes, and excess primer was not blotted off with an absorbent tissue paper.

[AP9]: Cognate to [AP8] except that 7 μl of primer was applied to each coupon of the adhesive joint.

9. Application of Dopes

Premixed Compositions of Dope Plus Crosslinker

Those compositions of dope plus crosslinker referred to below as being "premixed" were prepared using a dynamic mixing apparatus consisting of a 0.0625" diameter steel shaft supported at the proximal end in a compression bushing and rotating at 10,000 rpm in a Teflon® body bored to 0.078" diameter and open at the distal end. Dope and crosslinker were fed to the mixing apparatus using individual syringe pumps so that the feedrate of each component could be independently controlled. Each component entered the mixing chamber through it's own port located near the proximal end. The active length of the mixing chamber distal to the inlet ports was 1.28". The output of the mixing apparatus was applied directly to the 1 cm×1 cm surfaces of the intended joint on the test coupons.

GRG system [AD1]: All operations of this procedure were conducted at ambient room temperature of approximately 23° C. Two test coupons and a microscope slide were placed on a glass plate, the coupons covered with a sheet of plastic film to prevent evaporation of moisture, equilibrated to room temperature, and the assembly tared. Glutaraldehyde (2 μL, 25% w/w) was distributed evenly over the 1 cm×1 cm area of the intended adhesive joint on one test coupon using a P-20 Pipetman®. GRG dope [PD1] (10 μL) was applied evenly over the glutaraldehyde on the first coupon using a P-20 Pipetman®. The joint was assembled and then covered with the sheet of plastic film to retard evaporation of moisture. The microscope slide was placed on top of the plastic film and the joint. This whole assembly was placed onto a balance and a force of 2000±250 g was applied to the joint by hand for one minute. A 100 g weight was placed on top of the microscope slide.

GRF system [AD2]: All operations of this procedure were conducted in a 37° C. warm room. Two test coupons and a microscope slide were placed on a glass plate, the coupons covered with a sheet of plastic film to prevent evaporation of moisture, equilibrated to 37° C., and the assembly tared. GRF dope [PD2] (~10 μL) was troweled onto the 1 cm×1 cm area of the intended joint on one test coupon using a flat bladed stainless steel spatula. Formaldehyde (1 μL, 37% w/w) was uniformly distributed over the GRF dope on the first coupon using a P-20 Pipetman®. The joint was assembled and then covered with the sheet of plastic film to retard evaporation of moisture. The microscope slide was placed on top of the plastic film and the joint. This whole assembly was placed onto a balance and a force of 1500±250 g was applied to the joint by hand for 20 seconds. A 100 g weight was placed on top of the microscope slide.

SELP8K/glutaraldehyde system [AD3]: All operations of this procedure were conducted at ambient room temperature of approximately 23° C. Two test coupons and a microscope slide were placed on a glass plate, the coupons covered with a sheet of plastic film to prevent evaporation of moisture, equilibrated to room temperature, and the assembly tared. SELP8K dope [PD3] (5 μL per coupon) was uniformly distributed using a P-20 Pipetman® over the 1 cm×1 cm area intended for the joint. Glutaraldehyde (3.3 μL, 1.0 M) was uniformly distributed over the dope on one coupon. The joint was assembled and then covered with the sheet of plastic film to retard evaporation of moisture. The microscope slide was placed on top of the plastic film and the joint. A 100 g weight was placed on top of the microscope slide.

SELP0K-CS1 [PD4] system [AD4]: All the operations of this procedure were conducted at ambient room temperature of approximately 23° C. The dope and crosslinker were premixed. The flowrate of [PD4] dope was 22.54 ml/hr, and the flowrate of the HMDI was 0.67 ml/hr. The ratio of isocyanate groups from the HMDI to the amino groups from the [PD4] dope was approximately 10:1. Two test coupons and a microscope slide were placed on a glass plate, the coupons covered with a sheet of plastic film to prevent evaporation of moisture, equilibrated to room temperature, and the assembly tared. A hemispherical droplet, about 5 mm in diameter, of the premixed components was applied to each of the two test coupons. A gentle troweling motion with a flat bladed stainless steel spatula was used to uniformly distribute the droplet over the 1 cm×1 cm area intended for the joint. The joint was assembled and then covered with the sheet of plastic film to retard evaporation of moisture. The microscope slide was placed on top of the plastic film and the joint. This whole assembly was placed onto a tared balance and a force of 1500±250 g was applied to the joint by hand for one minute. A 100 g weight was place on top of the microscope slide.

SELP0K-CS1 [PD5] system [AD5]: Cognate to [AD4] except the flowrate of [PD5] dope was 22.39 mL/hr, and the flowrate of the IMP was 0.83 mL/hr The ratio of isocyanate groups from the IMP to the amino groups from the [PD5] dope was approximately 10:1.

TISSEEL [PD6] system [AD6]: All of the operations of this procedure were conducted in a 37° C. warm room. Two test coupons and a microscope slide were placed on a glass plate, the coupons covered with a sheet of plastic film to prevent evaporation of moisture, equilibrated to 37° C., and the assembly tared. A P-20 Pipetman® was used to apply the TISSEEL solution [PD6] (20 μL) to one coupon and the Thrombin 4 solution (20 μL) to the second coupon. Care was taken to uniformly distributed the solutions across the 1 cm×1 cm area intended for the joint. The joint was assembled and then covered with the sheet of plastic film to retard evaporation of moisture. The microscope slide was placed on top of the plastic film and the joint. This whole assembly was placed onto a balance and a force of 1500±250 g was applied to the joint by hand for one minute. A 100 g weight was then placed on top of the microscope slide.

SELP0K-CS1 [PD7] system [AD7]: All of the operations of this procedure were conducted in a 37° C. warm room. Two test coupons and a microscope slide were placed on a glass plate, the coupons covered with a sheet of plastic film to prevent evaporation of moisture, equilibrated to 37° C., and the assembly tared. SELP0K-CS1 dope [PD7] (15 μL) was applied using a P-20 Pipetman® to each coupon over the 1 cm×1 cm area intended for the joint, for a total of 30 μL. The dope was aggressively worked into the surface of the coupons using approximately 30 to 40 strokes with a flat bladed stainless steel spatula. IMP (2 μL) was then applied to both the coupons using a P-20 Pipetman® in a pattern of streaks: three equally spaced parallel streaks on one coupon and an "X"-shaped pattern of two streaks on the second coupon. The approximate mole ratio of isocyanate groups form the IMP to the amino groups from the SELP0K-CS1 was 18:1. The joint was assembled and covered with the sheet of plastic film to retard the evaporation of moisture. The microscope slide was placed on top of the plastic film and the joint. This whole assembly was placed onto a balance and a force of 1500±250 g was applied to the joint by hand for one minute. A 100 g weight was then placed on top of the microscope slide.

SELP0K-CS1 [PD8] system [AD8]: Cognate to [AD7], except SELP0K-CS1 dope [PD8] was used.

SELP0K-CS1 [PD4] system [AD9]: Cognate to [AD4], except the premix was aggressively worked into the surface of the coupons using approximately 30 to 40 strokes with a flat bladed stainless steel spatula.

SELP0K-CS1 [PD5] system [AD10]: Cognate to [AD5], except the flowrates for the SELP0K-CS1 dope [PD5] was 22.72 mL/hr and the flowrate for the IMP was 0.50 mL/hr. The ratio of isocyanate groups from the IMP to the amino groups from the [PD5] dope was approximately 6:1.

SELP0K-CS1 [PD5] system [AD11]: Cognate to [AD5], except the flowrates for the SELP0K-CS1 dope [PD5] was 22.97 mL/hr and the flowrate for IMP was 0.25 mL/hr. The ratio of isocyanate groups from the IMP to the amino groups from the [PD5] dope was approximately 3:1.

SELP0K-CS1 [PD5] system [AD12]: Cognate to [AD5], except the flowrates for the SELP0K-CS1 dope [PD5] was 23.13 mL/hr and the flowrate for IMP was 0.08 mL/hr. The ratio of isocyanate groups from the IMP to the amino groups from the [PD5] dope was approximately 1:1.

SELP0K-CS1 [PD9] system [AD13]: Cognate to [AD4] except that the flowrate for the SELP0K-CS1 dope was 11.28 mL/hr and the flowrate for HMDI was 0.337 mL/hr. The ratio of isocyanate groups from the HMDI to the amino groups from the [PD9] dope was approximately 10:1, but the residence time in the dynamic mixing apparatus was doubled 10. Curing Conditions

[C1]—The joint was permitted to cure at 23° C. for 30 minutes

[C2]—The joint was permitted to cure at 37° C. for 60 minutes

[C3]—The joint was permitted to cure at 37° C. for 30 minutes

[C4]—The joint was permitted to cure at 37° C. for 30 to 40 minutes.

[C5]—The joint was permitted to cure at 37° C. for 15 to 20 minutes.

11. Lap Shear Tensile Testing

Unless otherwise indicated, lap shear tests were conducted by carrying out the following steps:

(1) A uniform set of test coupons were selected.

(2) The solution of primer was applied to the surfaces of the joint.

(3) The dope and crosslinker was applied to the surfaces of the joint.

(4) The lap joint was assembled and cured.

(5) The strength of the lap joint was measured on an Instron tensile testing machine.

(6) The above steps were repeated without application of primer.

(7) The improvement of strength in the presence of primer was reported as an enhancement factor.

The lap shear tensile testing was conducted using an Instron Mini-55 tensile testing machine with pneumatic grips, using a ±500N (±0.5% of full scale) load cell, and at a crosshead speed of 25 mm/min. Testing was conducted at ambient room temperature and humidity.

Paper mounting frames were fabricated by cutting a 1"×1" square hole in the center of a 2"×2" square of standard glassine weighing paper. The lap joint specimen was affixed across the opening in the paper frame using adhesive tape. The dimensions of the joint were measured using a ruler. The use of a mounting frame facilitated accurate alignment of the test specimen in the pneumatic grips of the testing machine. Once the specimen was secured in the grips, the two sides of the mounting frame parallel to the specimen were cut, the gage length and load initialized, and the test started. The test was stopped shortly after the joint failed. The data acquisition rate was 4 samples per second. A file containing specimen identification, load, gage length, and duration was saved to disk. The lap shear tensile strength was calculated by dividing the highest load recorded for the specimen by the calculated area of the joint. Means and standard deviations for multiple measurement were calculated using standard methods.

Results

A. Identification of the Site of Mechanical Failure of a Tissue Bond.

In an attempt to develop novel tissue adhesive and sealant systems using the SELP0K-CS1 protein and isocyanate crosslinkers, techniques for increasing the mechanical strength of bonded tissue joints were examined. As part of this effort, rat skin test coupons were bonded with a SELP0K-CS1/isocyanate tissue adhesive, the coupons were T-peeled to induce partial debonding, the tissue samples were fixed, stained, microtomed and the sections mounted for histological examination. Microscopic examination of the mounted sections evidenced that the mechanical failure of the glued joints occurred not within the crosslinked adhesive matrix itself, but rather at the interface between the crosslinked adhesive matrix and the skin coupon. Thus, it is believed that the weakest component of the bond between the tissues was at the interface between the crosslinked adhesive matrix and one or more proteins present in the tissue.

B. Use of Primer Molecules to Enhance the Strength of the Adhesive Matrix/Tissue Protein Interface.

In an attempt to identify novel methods for enhancing the mechanical performance of tissue adhesives by increasing the strength of the adhesive matrix/tissue-associated protein interface, lap shear tensile testing as described above was performed with a variety of different combinations of adhesive matrix precursors, crosslinkers, primers, methods of primer preparation, methods of applying the primers, dopes, methods of applying the dopes and curing agents. The results from these experiments are presented in Table 1 wherein each of the above described variables are indicated by their codes as presented above and the number of experiments performed per case is shown in parentheses.

TABLE I

| Case | Test Coupon | Adhesive Matrix Precursor | Crosslinker | Primer ID [P#] Prep Primer [PP#] Appl'n Primer [AP#] | Prep Dope [PD#] Appl'n Dope [AD#] Cure [C#] | Lap Shear Tensile x ± σ (n) [g/cm²] | Enhancement |
|---|---|---|---|---|---|---|---|
| 1 | [CP1] | Gelatin | GA | none | [PD1], [AD1], [C1] | 296 ± 65 (15) | — |
| 2 | [CP1] | Gelatin | GA | [P10], [PP1], [AP3] | [PD1], [AD1], [C1] | 440 ± 52 (4) | 1.49 X |
| 3 | [CP1] | Gelatin | FA | none | [PD2], [AD2], [C3] | 670 ± 138 (6) | — |
| 4 | [CP1] | Gelatin | FA | [P10], [PP1], [AP4] | [PD2], [AD2], [C3] | 953 ± 235 (5) | 1.42 X |
| 5 | [CP1] | SELP8K | GA | none | [PD3], [AD3], [C2] | 143 ± 40 (6) | — |
| 6 | [CP1] | SELP8K | GA | [P10], [PP1], [AP3] | [PD3], [AD3], [C2] | 393 ± 89 (6) | 2.75 X |
| 7 | [CP1] | SELP8K | GA | [P2], [PP1], [AP3] | [PD3], [AD3], [C2] | 272 ± 73 (6) | 1.90 X |
| 8 | [CP1] | SELP8K | GA | [P11], [PP1], [AP3] | [PD3], [AD3], [C2] | 242 (1) | 1.69 X |
| 9 | [CP1] | SELP8K | GA | [P4], [PP1], [AP3] | [PD3], [AD3], [C2] | 229 (1) | 1.60 X |
| 10 | [CP1] | SELP8K | GA | [P12], [PP1], [AP3] | [PD3], [AD3], [C2] | 225 (1) | 1.57 X |
| 11 | [CP1] | SELPOK-CS1 | HMDI | none | [PD4], [AD4], [C4] | 452 ± 99 (12) | — |
| 12 | [CP1] | SELPOK-CS1 | HMDI | [P1], [PP1], [AP1] | [PD4], [AD4], [C4] | 1581 ± 157 (9) | 3.50 X |
| 13 | [CP1] | SELPOK-CS1 | HMDI | [P2], [PP1], [AP1] | [PD4], [AD4], [C4] | 972 (1) | 2.15 X |
| 14 | [CP1] | SELPOK-CS1 | HMDI | [P3], [PP1], [AP1] | [PD4], [AD4], [C4] | 958 (1) | 2.12 X |
| 15 | [CP1] | SELPOK-CS1 | HMDI | [P6], [PP1], [AP1] | [PD4], [AD4], [C4] | 1153 (1) | 2.55 X |
| 16 | [CP1] | SELPOK-CS1 | IMP | none | [PD5], [AD5], [C4] | 422 (1) | — |
| 17 | [CP1] | SELPOK-CS1 | IMP | [P1], [PP1], [AP1] | [PD5], [AD5], [C4] | 2029 (1) | 4.81 X |
| 18 | [CP1] | SELPOK-CS1 | IMP | none | [PD5], [AD10], [C4] | 421 (1) | — |
| 19 | [CP1] | SELPOK-CS1 | IMP | [P1], [PP1], [AP1] | [PD5], [AD10], [C4] | 2353 (1) | 5.59 X |
| 20 | [CP1] | SELPOK-CS1 | IMP | none | [PD5], [AD11], [C4] | 463 (1) | — |
| 21 | [CP1] | SELPOK-CS1 | IMP | [P1], [PP1], [AP1] | [PD5], [AD11], [C4] | 2013 (1) | 4.35 X |
| 22 | [CP1] | SELPOK-CS1 | IMP | none | [PD5], [AD12], [C4] | 274 (1) | — |
| 23 | [CP1] | SELPOK-CS1 | IMP | [P1], [PP1], [AP1] | [PD5], [AD12], [C4] | 1241 (1) | 4.53 X |
| 24 | [CP1] | Fibrin | F XIIIa | none | [PD6], [AD6], [C4] | 264 ± 34 (3) | — |
| 25 | [CP1] | Fibrin | F XIIIa | [P4], [PP1], [AP1] | [PD6], [AD6], [C4] | 1954 ± 40 (2) | 3.61 X |
| 26 | [CP1] | Fibrin | F XIIIa | [P5], [PP1], [AP1] | [PD6], [AD6], [C4] | 818 ± 198 (2) | 3.10 X |
| 27 | [CP1] | Fibrin | F XIIIa | [P7], [PP1], [AP1] | [PD6], [AD6], [C4] | 1217 ± 57 (3) | 4.61 X |
| 28 | [CP1] | Fibrin | F XIIIa | [P8], [PP1], [AP1] | [PD6], [AD6], [C4] | 1117 ± 337 (3) | 4.21 X |
| 29 | [CP1] | Fibrin | F XIIIa | [P9], [PP1], [AP1] | [PD6], [AD6], [C4] | 717 ± 7 (2) | 2.72 X |
| 30 | [CP1] | SELPOK-CS1 | IMP | none | [PP7], [AD7], [C5] | 1772 ± 394 (5) | — |
| 31 | [CP1] | SELPOK-CS1 | IMP | [P1], [PP9], [AP7] | [PD8], [AD8], [C5] | 2699 ± 362 (5) | 1.52 X |
| 32 | [CP1] | SELPOK-CS1 | HMDI | none | [PD4], [AD9], [C4] | 763 ± 95 (3) | — |
| 33 | [CP1] | SELPOK-CS1 | HMDI | [P21], [PP3], [AP5] | [PD4], [AD9], [C4] | 1440 ± 41 (2) | 1.89 X |
| 34 | [CP1] | SELPOK-CS1 | HMDI | [P21], [PP4], [AP5] | [PD4], [AD9], [C4] | 1505 ± 382 (2) | 1.97 X |
| 35 | [CP1] | SELPOK-CS1 | HMDI | [P21], [PP5], [AP5] | [PD4], [AD9], [C4] | 1577 (1) | 2.07 X |
| 36 | [CP1] | SELPOK-CS1 | HMDI | [P21], [PP6], [AP5] | [PD4], [AD9], [C4] | 1055 ± 8 (2) | 1.38 X |
| 37 | [CP1] | SELPOK-CS1 | HMDI | [P19], [PP7], [AP6] | [PD4], [AD9], [C4] | 1023 ± 61 (2) | 1.34 X |
| 38 | [CP1] | SELPOK-CS1 | HMDI | [P20], [PP8], [AP6] | [PD4], [AD9], [C4] | 1130 ± 431 (8) | 1.48 X |
| 39 | [CP1] | SELPOK-CS1 | HMDI | [P18], [PP2], [AP6] | [PD4], [AD9], [C4] | 1398 (1) | 1.83 X |
| 40 | [CP1] | SELPOK-CS1 | HMDI | [P5], [PP2], [AP6] | [PD4], [AD9], [C4] | 1523 (1) | 2.00 X |
| 41 | [CP1] | SELPOK-CS1 | HMDI | [P9], [PP2], [AP6] | [PD4], [AD9], [C4] | 1675 (1) | 2.20 X |
| 42 | [CP1] | SELPOK-CS1 | HMDI | [P4], [PP2], [AP6] | [P04], [AD9], [C4] | 1524 (1) | 2.00 X |
| 43 | [CP1] | SELPOK-CS1 | HMDI | [P1], [PP1], [AP2] | [PD4], [AD9], [C4] | 1821 (1) | 2.39 X |
| 44 | [CP1] | SELPOK-CS1 | HMDI | [P10], [PP1], [AP2] | [PD4], [AD9], [C4] | 1396 (1) | 1.82 X |
| 45 | [CP2t] | SELPOK-CS1 | HMDI | none | [PD9], [AD13], [C4] | 54 (1) | — |
| 46 | [CP2t] | SELPOK-CS1 | HMDI | [P22], [PP10], [AP8] | [PD9], [AD13], [C4] | 225 ± 21 (2) | 4.17 X |
| 47 | [CP2p] | SELPOK-CS1 | HMDI | none | [PD9], [AD13], [C4] | 32 (1) | — |
| 48 | [CP2p] | SELPOK-CS1 | HMDI | [P22], [PP10], [AP8] | [PD9], [AD13], [C4] | 117 ± 9 (2) | 3.34 X[a] |
| 49 | [CP2d] | SELPOK-CS1 | HMDI | none | [PD11], [AD13], [C4] | 33 (1) | — |
| 50 | [CP2d] | SELP0K-CS1 | HMDI | [P23], [PP1], [AP9] | [PD11], [AD13], [C4] | 78 (1) | 2.36 X |
| 51 | [CP2d] | SELPOK-CS1 | HMDI | [P24], [PP1], [AP9] | [PD11], [AD13], [C4] | 222 (1) | 6.73 X |
| 52 | [CP2d] | SELPOK-CS1 | HMDI | [P25], [PP1], [AP9] | [PD11], [AD13], [C4] | 45 (1) | 1.36 X |
| 53 | [CP3] | SELPOK-CS1 | HMDI | none | [PD10], [AD13], [C4] | <60 (2) | — |
| 54 | [CP3] | SELPOK-CS1 | HMDI | [P1], [PP1], [AP8] | [PD10], [AD13], [C4] | 1492 ± 331 (2) | 24 X |
| 55 | [CP4] | SELPOK-CS1 | HMOI | none | [PD10], [AD13], [C4] | 470 ± 41 (3) | — |
| 56 | [CP4] | SELPOK-CS1 | HMOI | [P1], [PP1], [AP8] | [PD10], [AD13], [C4] | 622 ± 181 (4) | 1.32 X |
| 57 | [CP5] | SELPOK-CS1 | HMDI | none | [PD10], [AD13], [C4] | 114 (1) | — |
| 58 | [CP5] | SELPOK-CS1 | HMDI | [P1], [PP1], [AP8] | [PD10], [AD13], [C4] | 476 ± 36 (3) | 4.18 X |

[a]The tabs of the lap joint failed under load before the joint itself. Therefore, this is a minimum enhancement.

The results presented in Table 1 demonstrate that a variety of different primer molecules which are capable of interacting with and altering the physical characteristics of protein(s) present in the test coupons significantly enhance the mechanical performance of a variety of different tissue adhesive matrix compositions. For example, case numbers 1–4 presented in Table I demonstrate that the Acid Red 97 primer molecule [P10] functions to significantly enhance the mechanical performance of a gelatin adhesive matrix when either a glutaraldehyde or formaldehyde crosslinker is employed. These results demonstrate that natural proteins (i.e., gelatin) may be employed in association with a chemical crosslinker (e.g., glutaraldehyde or formaldehyde) and a primer molecule to provide for improved tissue adhesive or sealant properties.

Cases 5–10 presented in Table I demonstrate that the Evan's Blue [P2], Cibacron Blue 3GA [P4], Acid Red 97 [P10], Trypan Blue [P11] and New Coccine [P12] primer molecules were all capable of significantly enhancing the mechanical performance of a SELP8K tissue adhesive matrix which employed a glutaraldehyde crosslinker. Thus, these results demonstrate that primer molecules are also useful for enhancing the mechanical properties of tissue adhesives or sealants based upon recombinantly produced proteins and chemical crosslinkers.

Cases 11–15 and 32–44 presented in Table I demonstrate that the Brilliant Blue G [P1], Evan's Blue [P2], Chicago Sky Blue 6B [P3], Cibacron Blue 3GA [P4], Cibacron Brilliant Yellow 3G-P [P5], Brilliant Blue R [P6], Cibacron Brilliant Red 3B-A [P9], Acid Red 97 [P10], Orange G [P18], Urea [P19], Tisseel® Fibrinogen [P20] and SELP0K-CS1 [P21] primer molecules all provided a significant enhancement in the mechanical performance of a SELP0K-CS1 adhesive matrix which employed a 1,6-diisocyanatohexane crosslinker. As shown in Table I, numerous different elements of the experiments were varied, none of which inhibited the ability of the primer molecules from enhancing the mechanical performance of the tissue bond produced.

The use of urea as a primer molecule in case number 37 is interesting in that it implies that one mechanism of action is related to the fact that urea is a known chaotropic agent which is routinely used to solubilize and denature many proteins. As such, urea swells and unravels the structure of the native collagen protein in the tissue, thereby making it more accessible to interact with the components of a tissue adhesive or sealant which will crosslink to form the adhesive matrix.

Case number 38 employs fibrinogen (i.e., a protein which functions as a clotting agent) as a primer molecule which provides for a significant increase in the mechanical performance of the tissue adhesive matrix. Fibrinogen, which has evolved to interact strongly with many different surfaces of the body (including collagen), may function to make the surface of the underlying tissue collagen more physically compatible with the components of the adhesive matrix, e.g., more wettable by the components, thereby allowing the tissue adhesive or sealant to more efficiently interact with the collagen and, in turn, form a stronger bond.

Cases 16–23, 30 and 31 presented in Table I demonstrate that the Brilliant Blue G [P1] primer molecule is capable of providing a significant enhancement in the mechanical performance of a SELP0K-CS1 adhesive matrix which employed a 4-isocyanatomethylphenyl-3-isocyanatopropanate (IMP) crosslinker. Interestingly, these results also demonstrate that not only may the tissue be pretreated with the primer molecules followed by application of the dope and crosslinker, but also the primer molecules may be pre-mixed with the dope and crosslinker prior to application to the tissue without adversely affecting the ability of the primer molecule to enhance the mechanical properties of the tissue bond.

Cases 24–29 presented in Table I demonstrate that the Cibacron Blue 3GA [P4], Cibacron Brilliant Yellow 3G-P [P5], Lissamine Green B [P7], Acid Blue 92 [P8] and Cibacron Brilliant Red 3B-A [P9] primer molecules are all capable of significantly enhancing the mechanical performance of a fibrin-based adhesive matrix which employed a Factor XIIIa crosslinker. These results demonstrate that not only may chemical crosslinkers be employed in association with protein adhesive matrices, but enzymatic crosslinkers (e.g., Factor XIIIa) may be employed as well.

Finally, cases 45–58 presented in Table I demonstrate that various primer molecules are capable of significantly enhancing the mechanical performance of a SELP0K-CS1-based adhesive matrix which employed an HMDI crosslinker on a variety of different test tissues including myocardium (a tissue which possesses abundant levels of actin and myosin), bone, tendon and articular cartilage. As such, the present invention is applicable to enhancing the mechanical performance of a variety of adhesive matrices on a variety of different mammalian tissues.

The foregoing description details specific methods which can be employed to practice the present invention. Having detailed such specific methods, those skilled in the art will well enough know how to devise alternative reliable methods at arriving at the same results in using the fruits of the present invention. Thus, however detailed the foregoing may appear in text, it should not be construed as limiting the overall scope thereof; rather, the ambit of the present invention is to be determined only by the lawful construction of the appended claims. All documents cited herein are expressly incorporated herein by reference.

What is claimed is:

1. A method of adhering a tissue adhesive to a tissue, said method comprising:

applying to said tissue (a) a primer molecule and (b) a tissue adhesive, said primer molecule being capable of physically interacting with a component present in said tissue and thereby rendering said tissue capable of forming a bonded interface with said tissue adhesive where said primer molecule is selected from the group consisting of fibronectin, fibrinogen and albumin.

2. The method according to claim 1, wherein said component present in said tissue is a protein.

3. A method of maintaining separated tissues in proximate relationship, said method comprising:

applying to said separated tissues (a) a primer molecule and (b) a tissue adhesive, said primer molecule being capable of physically interacting with a component present in said separated tissues and thereby rendering said separated tissue capable of forming a bonded interface with said tissue adhesive where said primer molecule is selected from the group consisting of fibronectin, fibrinogen and albumin, and wherein (a) and (b) are applied in an amount effective to maintain said separated tissues in proximate relationship when said separated tissues are brought into proximate relationship.

4. The method according to claim 3 which maintains said separated tissues in proximate relationship with greater bond strength than when said tissue adhesive is employed in the absence of said primer molecule.

5. The method according to claim 3, wherein said primer molecule is applied to said separated tissues before said tissue adhesive is applied to said separated tissues.

6. The method according to claim 3, wherein said tissue adhesive and said primer molecule are combined prior to application to said separated tissues.

7. The method according to claim 3, wherein said applying occurs prior to bringing said separated tissues into proximate relationship.

8. The method according to claim 3, wherein said tissue adhesive comprises a polypeptide that is capable of being crosslinked.

9. The method according to claim 3, wherein said separated tissues comprise skin, bone, tendon, muscle or cartilage.

10. The method according to claim 3, wherein said component present in said separated tissue with which said primer molecule physically interacts is a protein selected from the group consisting of collagen, actin and myosin.

11. A method of sealing a defect in tissue, said method comprising:

applying to said defect (a) a primer molecule and (b) a tissue sealant, said primer molecule being capable of physically interacting with a protein present in said tissue and thereby rendering said tissue capable of forming a bonded interface with said tissue sealant where said primer is selected from the group consisting of fibronectin, fibrinogen and collagen, wherein (a) and (b) are applied to said defect in an amount effective to seal said defect.

12. The method according to claim 11, wherein said primer molecule is applied to said defect before said tissue sealant is applied to said defect.

13. The method according to claim 11, wherein said tissue sealant and said primer molecule are combined prior to application to said defect.

14. The method according to claim 11, wherein said defect is a result of a surgical procedure.

15. A composition of matter useful for forming a bonded interface with a tissue when said composition of matter is applied to said tissue, said composition of matter comprising:
  (a) a tissue adhesive or sealant; and
  (b) a primer molecule which is capable of physically interacting with a component present in said tissue and thereby rendering said tissue capable of forming a bonded interface with said tissue adhesive or sealant said primer molecule being selected from the group consisting of fibronectin, fibrinogen and collagen.

16. A kit comprising the composition of matter according to claim 15.

* * * * *